United States Patent
Nakamura et al.

(10) Patent No.: US 8,718,228 B2
(45) Date of Patent: May 6, 2014

(54) PHASE GRATING USED FOR X-RAY PHASE IMAGING, IMAGING APPARATUS FOR X-RAY PHASE CONTRAST IMAGE USING PHASE GRATING, AND X-RAY COMPUTED TOMOGRAPHY SYSTEM

(75) Inventors: Takashi Nakamura, Yokohama (JP); Aya Imada, Tokyo (JP); Hidenosuke Itoh, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 263 days.

(21) Appl. No.: 12/922,145

(22) PCT Filed: Mar. 12, 2009

(86) PCT No.: PCT/JP2009/055375
§ 371 (c)(1),
(2), (4) Date: Sep. 10, 2010

(87) PCT Pub. No.: WO2009/113726
PCT Pub. Date: Sep. 17, 2009

(65) Prior Publication Data
US 2011/0013743 A1    Jan. 20, 2011

(30) Foreign Application Priority Data
Mar. 13, 2008  (JP) ................................. 2008-064709

(51) Int. Cl.
*G21K 1/00*    (2006.01)
(52) U.S. Cl.
USPC ............................................ 378/36; 378/149
(58) Field of Classification Search
USPC ................ 378/19, 36, 62, 147, 149, 154, 155
See application file for complete search history.

(56) References Cited

U.S. PATENT DOCUMENTS

| | | | | |
|---|---|---|---|---|
| 4,419,585 A | * | 12/1983 | Strauss et al. | 250/505.1 |
| 4,651,002 A | * | 3/1987 | Anno | 250/336.1 |
| 5,606,589 A | * | 2/1997 | Pellegrino et al. | 378/154 |
| 5,812,629 A | | 9/1998 | Clauser et al. | |

(Continued)

FOREIGN PATENT DOCUMENTS

| | | |
|---|---|---|
| JP | H07-333396 A | 12/1995 |
| JP | 2006-163291 A | 6/2006 |
| JP | 2007-203066 A | 8/2007 |

OTHER PUBLICATIONS

International Preliminary Report on Patentability (IPRP) for PCT/JP2009/055375; (9 pages included).

*Primary Examiner* — Allen C. Ho
(74) *Attorney, Agent, or Firm* — Canon USA Inc. IP Division (57) ABSTRACT

A phase grating used for X-ray phase imaging is provided, in which a pitch can be narrowed by using a diffraction grating with a low aspect ratio. A phase grating used for X-ray phase imaging, characterized in that the phase grating includes a first diffraction grating in which a first projection part whose thickness is formed so that an in-coming X-ray transmits with a phase π-shifted, and a first aperture part with the same aperture width as a width of the first projection part are cyclically arranged, and a second diffraction grating in which a second projection part with the same width as a width of the first projection part, and a second aperture part with the same aperture width as the aperture width of the first aperture part are cyclically arranged, and the second diffraction grating is formed as displaced on the first diffraction grating.

15 Claims, 8 Drawing Sheets

(56) References Cited

U.S. PATENT DOCUMENTS

| | | | |
|---|---|---|---|
| 7,433,444 B2 * | 10/2008 | Baumann et al. | 378/62 |
| 7,486,770 B2 * | 2/2009 | Baumann et al. | 378/62 |
| 7,492,871 B2 * | 2/2009 | Popescu et al. | 378/145 |
| 7,522,698 B2 * | 4/2009 | Popescu et al. | 378/19 |
| 7,522,708 B2 * | 4/2009 | Heismann et al. | 378/145 |
| 7,564,941 B2 * | 7/2009 | Baumann et al. | 378/19 |
| 7,639,786 B2 * | 12/2009 | Baumann et al. | 378/145 |
| 7,920,676 B2 * | 4/2011 | Yun et al. | 378/86 |
| 7,924,973 B2 * | 4/2011 | Kottler et al. | 378/36 |
| 7,945,018 B2 * | 5/2011 | Heismann et al. | 378/62 |
| 7,949,095 B2 * | 5/2011 | Ning et al. | 378/62 |
| 7,983,381 B2 * | 7/2011 | David et al. | 378/4 |
| 8,009,796 B2 * | 8/2011 | Popescu et al. | 378/19 |
| 8,009,797 B2 * | 8/2011 | Ouchi et al. | 378/36 |
| 8,351,570 B2 * | 1/2013 | Nakamura et al. | 378/62 |
| 2007/0183579 A1 | 8/2007 | Baumann et al. | |
| 2007/0298533 A1 | 12/2007 | Yang et al. | |
| 2008/0002209 A1 | 1/2008 | Yaqoob et al. | |

* cited by examiner

PHASE GRATING USED FOR X-RAY PHASE IMAGING, IMAGING APPARATUS FOR X-RAY PHASE CONTRAST IMAGE USING PHASE GRATING, AND X-RAY COMPUTED TOMOGRAPHY SYSTEM

CROSS REFERENCE TO RELATED APPLCIATIONS

This application is a U.S. National Stage of International application No. PCT/JP2009/055375 filed on Mar. 12, 2009 which claims priority from Japanese Patent Application No. 2008-064709 filed on Mar. 13, 2008, the disclosures of which are hereby incorporated by reference herein in their entirety.

TECHNICAL FIELD

The present invention relates to a phase grating used for X-ray phase imaging, an imaging apparatus for an X-ray phase contrast image using the phase grating, and an X-ray computed tomography system.

BACKGROUND ART

Conventionally, an X-ray fluoroscopic imaging technique has been studied, which obtains a contrast image by utilizing the difference of X-ray absorption abilities. However, as an element becomes lighter, the X-ray absorption ability becomes smaller, resulting in a problem that enough contrast cannot be expected for biological soft tissue and soft material. In view of above mentioned problem, an imaging method which generates the contrast based on a phase shift of the X-ray has been studied in recent years. An imaging method using the Talbot interference is one of X-ray phase imaging methods utilizing such a phase contrast.

Figure 8:
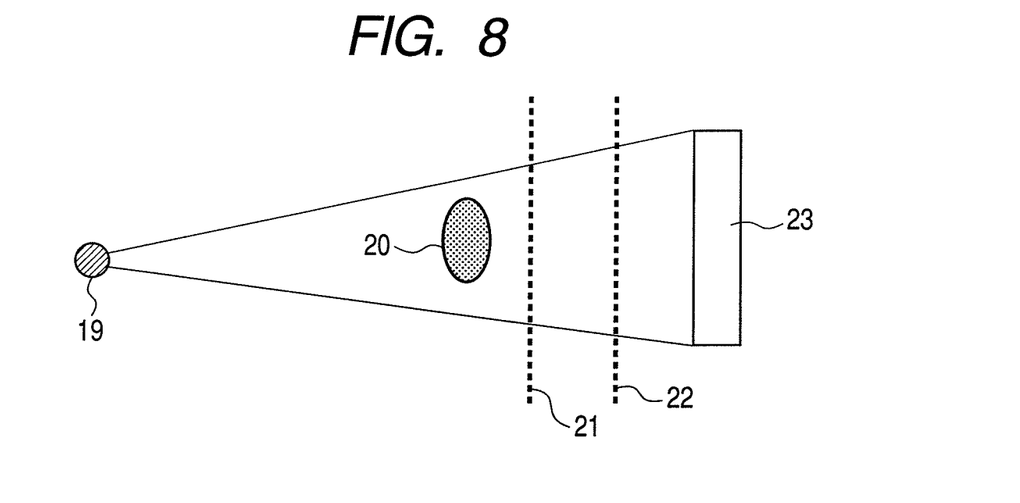
FIG. 8 is a diagram for describing a Talbot interferometer for obtaining an X-ray phase image, which is a conventional example.

FIG. 8 illustrates an exemplary configuration of the Talbot interference method. The imaging by the Talbot interference method needs at least an X-ray source 19 which can be spatially interfered, a phase-type diffraction grating 21 (hereinafter, described as phase grating) for cyclically modulating a phase of the X-ray, and a detector 23. An X-ray intensity distribution of the X-ray which can be spatially interfered, after it transmits through the phase grating 21, resembles the shape of the phase grating 21. When a spatial coherence length of the X-ray is larger than a pitch of the phase grating 21, a light-dark cyclic image with high contrast appears at a location of $(d^2/\lambda) \times a/8$. Here, "d" is a pitch of the phase grating 21, "$\lambda$" is a wavelength of the X-ray, and "a" is an odd integer. In the present specification, the pitch of the phase grating means a cycle in which the grating is arranged. The pitch of the phase grating may be a distance C between centers of one grating and other grating neighboring to the grating, or a distance C' between sides of two consecutive gratings, as illustrated in the schematic diagram of the phase grating shown in FIG. 9.

As described above, a Talbot effect is a phenomenon in which a light-dark cyclic image is cyclically formed at a specific distance between the phase grating 21 and the detector 23. This light-dark cyclic image is referred to as a self-image. When a test object 20 is located in front of the phase grating 21, the irradiated X-ray is refracted by the test object 20. Thus, a phase image of the test object 20 can be obtained by the detecting of the self-image which is formed by the X-ray refracted because of transmitting the test object 20. However, an X-ray image detector with high spatial resolution becomes necessary to detect the self-image generated with enough contrast. In such a case, an absorption grating 22 can be utilized, which is made of material absorbing the X-ray, and having a sufficient thickness. When absorption grating 22 is located in a location in which the self-image is formed, moiré fringes are generated by the overlapping of this self-image and the absorption grating 22. That is, information on the phase shift can be observed by the detector 23 as modification of the moiré fringes.

By the way, when it is necessary to observe in a high resolution, it is more desirable that the pitch of the phase grating 21 is smaller. On the other hand, as the phase grating, some thickness (height) becomes necessary to $\pi$-shift the phase of the X-ray. Meanwhile, as illustrated in a schematic diagram of FIG. 9, in the present specifications, the thickness (height) of the phase grating means the thickness (height) of a projection part which is a long side of the grating indicated by "B". A width of the projection part means a width indicated by "A" in the above FIG. 9. An aperture width of an aperture part means a distance between the projection parts, which is indicated by "A'" in the above FIG. 9.

Figure 9:
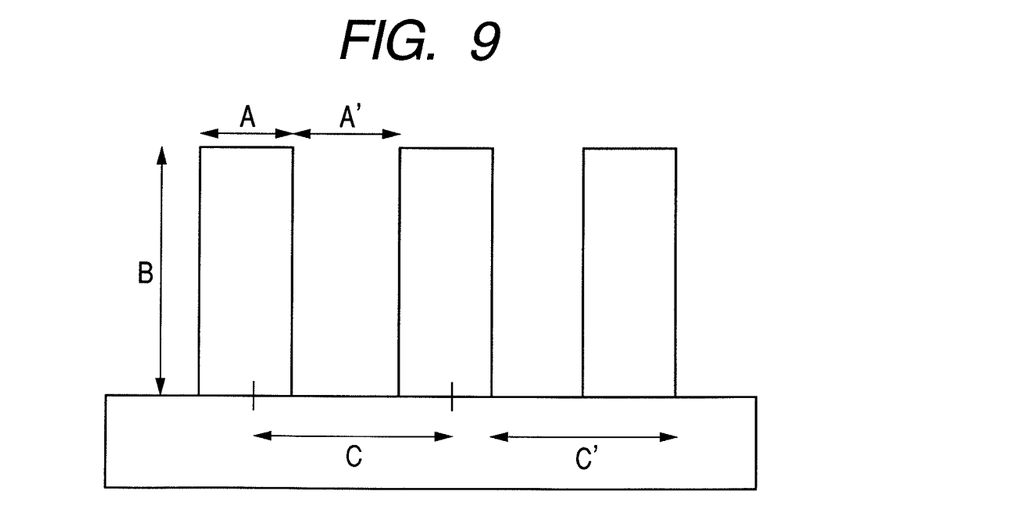
FIG. 9 is a schematic diagram for describing a pitch, a thickness (height) of a projection part, a width of the projection part, and an aperture width of the phase grating and the diffraction grating used for the X-ray phase imaging.
Figure 10:
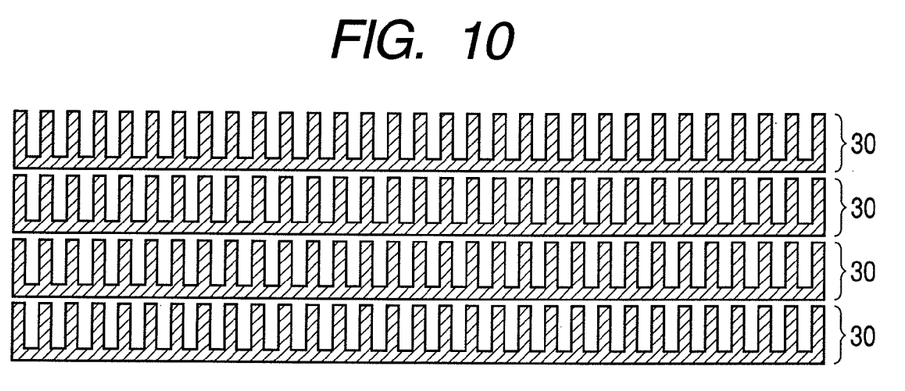
FIG. 10 is a diagram for describing US Patent Application Publication No. 2007/0183579 now U.S. Pat. No. 7,639,786 specifications, which is a conventional example.

"Aperture width" and "width of the projection part" of the phase grating are generally formed by 1:1. Here, when the pitch of the phase grating 21 is caused to be smaller to make the phase grating 21 with the high resolution, it is also necessary to downsize the width of the projection part and the aperture width. Thus, such a problem is induced that an aspect ratio becomes larger, which is defined by the thickness (height) of the projection part/the aperture width of the aperture part, or the thickness (height) of the projection part/the width of the projection part, so that it becomes difficult to make the phase grating 21. For example, when Si is used as material of the phase grating 21, the thickness necessary to $\pi$-shift the phase of the X-ray of 20 keV is approximately 29.2 μm. When the slit-like phase grating 21 is made, it is required to make the slit-like phase grating 21 with a pitch of approximately 2 μm, that is, the aperture width of 1 μm because of the desired resolution. In this case, the aspect ratio becomes approximately 30, resulting in that it is difficult to make the diffraction grating with a large area. Thus, in US Patent Application Publication No. 2007/0183579 (now U.S. Pat. No.: 7,639,786) specifications, a partial grating with the low aspect ratio is used to make the diffraction grating whose apparent aspect ratio is high. Specifically, as illustrated in FIG. 10, partial gratings 30, which can be easily made, with the lower aspect ratio are stacked in a virtual direction, thereby, the diffraction grating, whose apparent aspect ratio is high, is made.

SUMMARY OF THE INVENTION

In the above conventional example described in US Patent Application Publication No. 2007/0183579 (now U.S. Pat. No.: 7,639,786) specifications, by stacking the partial gratings 30 with the low aspect ratio, the diffraction grating is made, whose apparent height of the projection part is increased, resulting in the high aspect ratio. However, in the diffraction grating of US Patent Application Publication No. 2007/0183579 (now U.S. Pat. No.: 7,639,786) specifications, while the apparent aspect ratio is increased by multilayering the diffraction grating with the low aspect ratio the pitch is not downsized, but is the same size, so that the high resolution is not realized.

Under the consideration of the above problem, an object of the present invention is to provide the phase grating used for the X-ray phase imaging in which the pitch can be narrowed by using the diffraction grating with the low aspect. An object of the present invention is also to provide an imaging apparatus for an X-ray phase contrast image, in which the above phase grating is used, and an X-ray computed tomography system including such an imaging apparatus.

According to the present invention, it is possible to realize the phase grating used for the X-ray phase imaging in which the pitch can be narrowed by using the diffraction grating with the low aspect. Further, according to the present invention, it is possible to realize the imaging apparatus for the X-ray phase contrast image, in which the above phase grating is used, and the X-ray computed tomography system including the imaging apparatus.

Further features of the present invention will become apparent from the following description of exemplary embodiments with reference to the attached drawings.

DETAILED DESCRIPTION OF THE EMBODIMENTS

Next, exemplary embodiments of the present invention will be described.

A phase grating according to the present invention includes a first diffraction grating and a second diffraction grating. In the first diffraction grating, a first projection part whose thickness is formed so that an in-coming X-ray transmits with a phase π-shifted, and a first aperture part with the same aperture width as a width of the first projection part, are cyclically arranged. In the second diffraction grating, a second projection part with the same width as a width of the first projection part, and a second aperture part with the same aperture width as the aperture width of the first aperture part, are cyclically arranged. The second diffraction grating is displaced to be formed on the first diffraction grating. Meanwhile, in the phase grating according to the present invention, "same" means that an error in the production may be included in a range that the imaging can be executed by the Talbot interference method (hereinafter, the same as above).

Here, the thickness of the projection part means the thickness (height) of the projection part which is a long side of the grating indicated by "B" in FIG. 9. The width of the projection part means the width of the projection part which is a short side of the grating indicated by "A" in FIG. 9. The aperture width means a distance between the gratings indicated by "A'" in FIG. 9. The width "A" of the projection part and the aperture width "A'" are the same as each other.

Figure 1A:
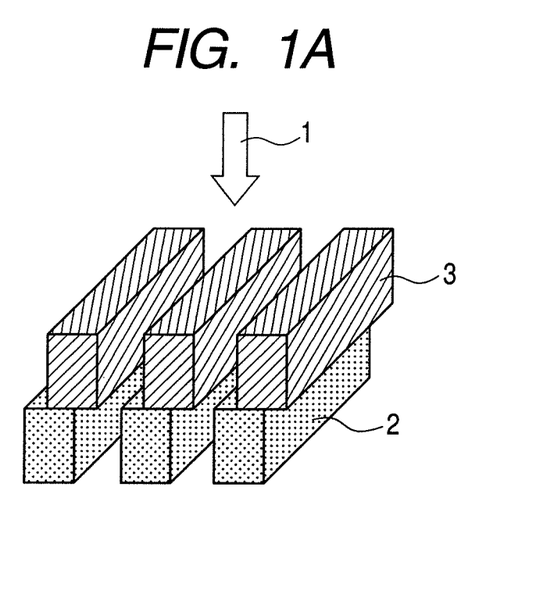
FIG. 1A is a view for describing an exemplary configuration of a one-dimensional phase grating used for X-ray phase imaging, in which two layers of line-like diffraction gratings are displaced as stacked mutually in an exemplary embodiment 1 of the present invention.
Figure 4A:
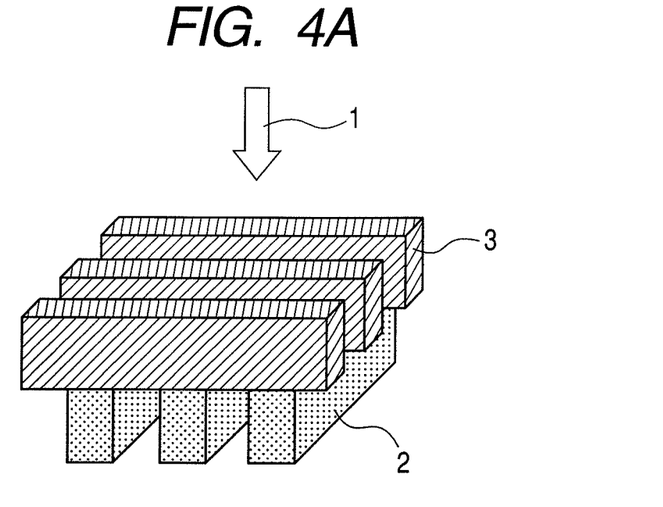
FIG. 4A is a view for describing an exemplary configuration of a two-dimensional phase grating used for the X-ray phase imaging, in which one layer of the two layers of the line-like diffraction gratings is stacked so as to be orthogonal to the other layer in an exemplary embodiment 2 of the present invention.

The second diffraction grating may be displaced to be formed on the first diffraction grating so that the first projection part and the second projection part do not completely correspond to each other (FIG. 1A). Here, a case that the first projection part and the second projection part completely correspond to each other means a case that an edge face of the first projection part and an edge face of the second projection part are on the same surface. Meanwhile, the edge face of the projection part means a face for defining the width of the projection part. That is, a cyclic direction in which the first projection part and the first aperture part of the first diffraction grating are arranged, and a cyclic direction in which the second projection part and the second aperture part of the second diffraction grating are arranged, may be the same as each other, alternatively, the second diffraction grating may be formed as displaced by ¼-pitch for the first diffraction grating. Further, the cyclic direction in which the first projection part and the first aperture part are arranged, and the cyclic direction in which the second projection part and the second aperture part are arranged may be orthogonal to each other (FIG. 4A).

Figure 3A:
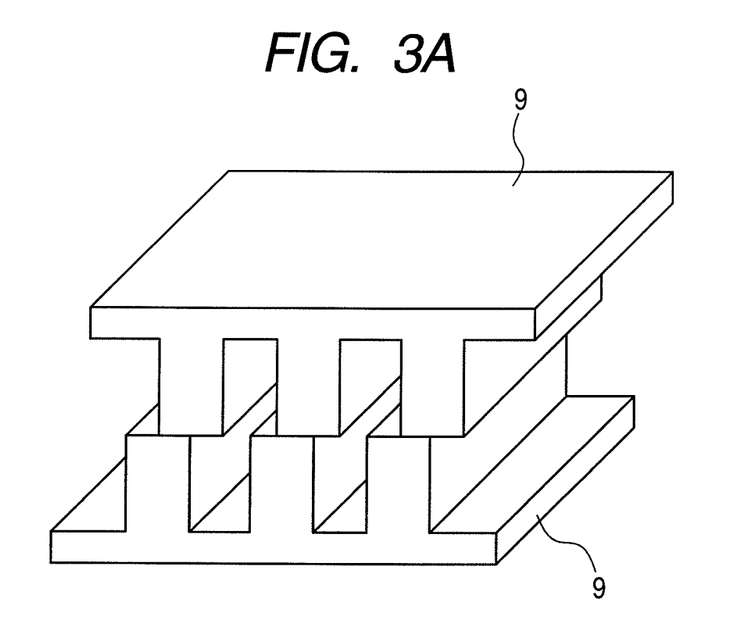
FIG. 3A is a view for describing an exemplary configuration in which the phase grating is formed so that projection parts of the two diffraction gratings face each other in the exemplary embodiment 1 of the present invention.
Figure 3B:
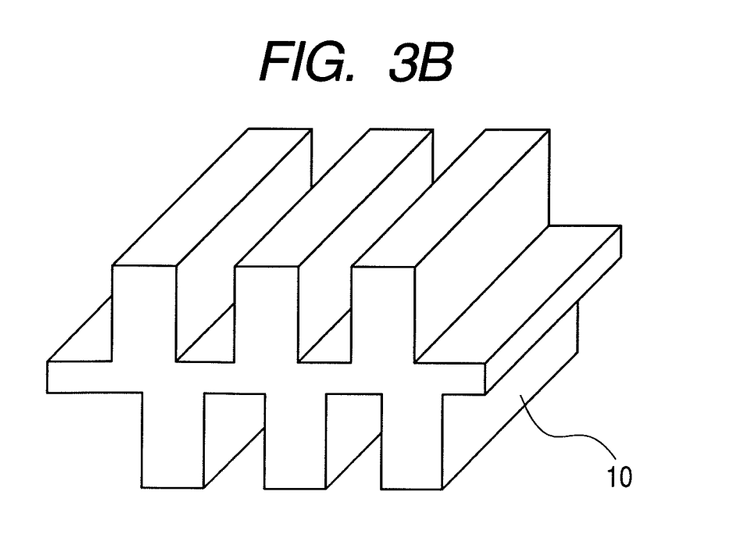
FIG. 3B is a view for describing an exemplary configuration in which the diffraction grating is used, which is formed by processing both sides of the substrate in the exemplary embodiment 1 of the present invention.

The first diffraction grating may be formed in one face side of the substrate, and the second diffraction grating may be formed in the other face side of the substrate as displaced by ¼-pitch (FIG. 3B).

Figure 5A:
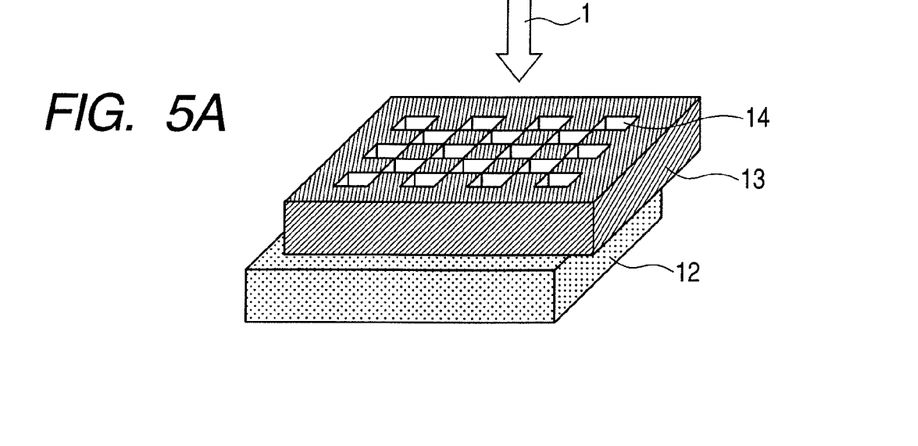
FIG. 5A is a view describing an exemplary configuration of the two-dimensional phase grating configured by stacking two layers of checker grating-like diffraction gratings in the exemplary embodiment 2 of the present invention.

The first diffraction grating may include the square-shaped first aperture part which is two-dimensionally arranged in a first direction and a second direction orthogonal to the first direction, and the second diffraction grating may include the square-shaped second aperture part which is two-dimensionally arranged in the first direction and the second direction. When such first and second diffraction gratings are used, the second diffraction grating may be formed on first diffraction grating as displaced by ¼-pitch in the first direction and the second direction respectively (FIG. 5A).

In another phase grating of the present invention, "n" pieces of the diffraction gratings are stacked. In each diffraction grating, the projection part whose thickness is formed so that the in-coming X-ray transmits with a phase π-shifted, and the aperture part with the same aperture width as a width of the projection part are cyclically and one-dimensionally arranged. The projection part of the m-th (m=2, 3, . . . n) diffraction grating is formed as displaced by 1/(2n)-pitch in a cyclic direction of a one-dimensional arrangement for the projection part of the (m−1)-th diffraction grating.

In the above-configured phase grating, an area in which the X-ray in-coming to the phase grating transmits with the phase π-shifted, and an area in which the X-ray in-coming to the phase grating transmits without the phase π-shifted are cyclically arranged, so that as compared with each diffraction grating, a pitch of an area, in which the phase of the X-ray is modulated, can be narrowed.

(Exemplary Embodiment 1)

An example of the phase grating according to the present invention will be described below.

In the exemplary embodiment 1, an exemplary configuration of a one-dimensional phase grating will be described, which is used for X-ray phase imaging with a structure in which a pitch is narrowed than each diffraction grating by stacking two layers of line-like diffraction gratings displayed in a cyclic direction for an in-coming X-ray. FIG. 1A illustrates the exemplary configuration of the one-dimensional phase grating in which a first diffraction grating 2 and a second diffraction grating 3 are displaced with respect to each other and stacked upon each other. In the one-dimensional phase grating of the present exemplary embodiment, the line-like diffraction grating means a structure in which line-like projection structures (projection parts) which are parallel to each other, and aperture parts with the same aperture width as a width of the projection part are cyclically arranged.

In the present exemplary embodiment, the projection part of the line-like diffraction grating includes the "width" in a direction perpendicular to a direction in which an X-ray 1 transmits, and the "thickness" in the same direction as the direction in which the X-ray transmits, and the thickness is formed so that the in-coming X-ray transmits with a phase π-shifted. When the above two layers of the line-like diffraction gratings are stacked, a second layer of diffraction grating 3 (second diffraction grating) is formed as displaced by ¼-pitch in the cyclic direction of a first layer of diffraction grating 2 (first diffraction grating).

Figure 1B:
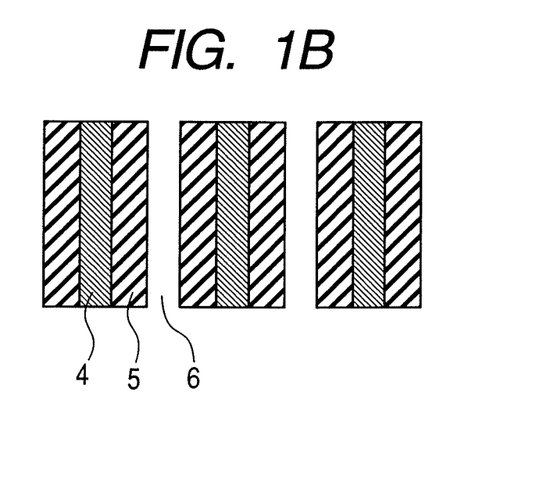
FIG. 1B is a view illustrating a phase difference of an X-ray transmitting the one-dimensional phase grating illustrated in FIG. 1A.

AS illustrated in FIG. 1A, the X-ray 1 in-comes from a direction perpendicular to a surface in which the projection part is arranged. In the X-ray in-coming and transmitting this one-dimensional phase grating, the phase of the X-ray, which does not transmit the projection part, is not changed, the phase of the X-ray, which transmits one layer of the projection part, is π-shifted, and the phase of the X-ray, which transmits two layer of the projection part, is 2π-shifted. In such a case, as illustrated in FIG. 1B, the phase of the X-ray transmitting the one-dimensional phase grating forms an area 6 in which the phase of the in-coming X-ray is not changed, an area 5 in which the phase is π-shifted, and an area 4 in which the phase is 2π-shifted. Here, the 2π-shifted phase of the X-ray transmitting the two layers of the projection part is the same as the phase of a part (a part in which the phase is 0-shifted), which does not transmit the projection part. As described above, in the X-ray phase grating obtained by multilayering the diffraction grating which causes the in-coming X-ray to transmit with the phase π-shifted, the pitch of an area, in which the phase of the X-ray is modulated, can be narrowed as compared with each diffraction grating. For example, the pitch of the diffraction grating with the two layer-structure illustrated in FIG. 1A becomes ½ of the pitch of the first or second diffraction grating. Meanwhile, in the above exemplary embodiment, the diffraction grating is stacked as displaced by ¼-pitch in the cyclic direction so that a width of the area of a phase difference π, and a width of the area of a phase difference 0 or 2π become equal to each other. However, when the diffraction grating is used as the phase grating, the above two areas may not be equal to each other. For example, when the width of the projection part and the aperture width are equal to each other in the first and second diffraction gratings, by displacing the projection part and the aperture part in stacking the both diffraction gratings, the pitch can be narrowed than the pitch of each diffraction grating. Meanwhile, as in the above exemplary embodiment, it is desirable that the width of the area of the phase difference π and the width of the area of the phase difference 0 or 2π are caused to be equal to each other in that an X-ray phase contrast image with high contrast can be obtained. Since a distance from an X-ray source to a detector is enough large, a difference between light-path lengths may be neglected.

Figure 2A:
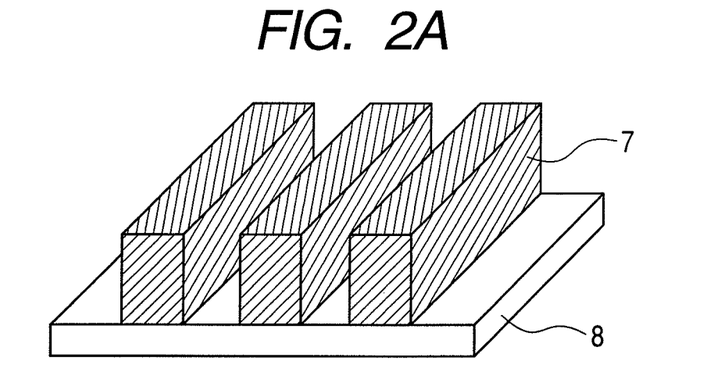
FIG. 2A is a view for describing an exemplary configuration of the diffraction grating in which material forming a substrate and material forming a projection part are different from each other in the exemplary embodiment 1 of the present invention.
Figure 2B:
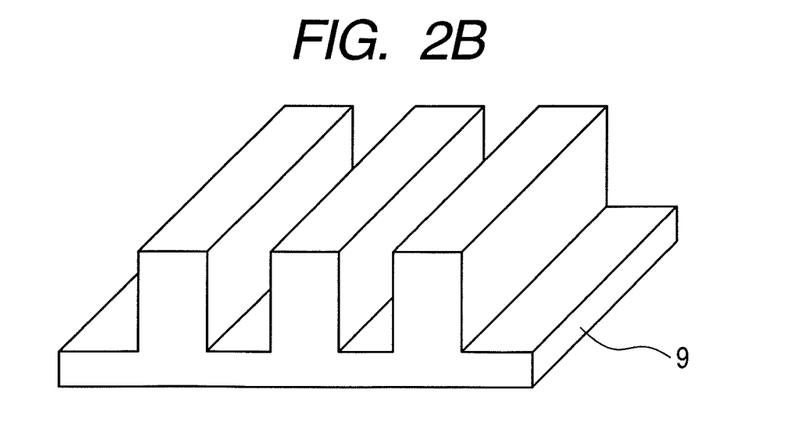
FIG. 2B is a view for describing an exemplary configuration in which the diffraction grating is formed by processing a part of the substrate in the exemplary embodiment 1 of the present invention.

Each diffraction grating configured in the above phase grating can be formed on a surface of the substrate, inside the substrate, or both. In such a case, in the diffraction grating, material forming a projection part 7 and material forming a projection part 8 may be different from each other (FIG. 2A), and the projection part may be formed by processing a part of the substrate (diffraction grating 9 of FIG. 2B). A structure of the diffraction grating illustrated in FIG. 2B is a non-penetration type, but may be a penetration type. Since the X-ray is not absorbed by the penetration type-substrate, the usage efficiency for the X-ray is improved. As illustrated in FIG. 3A, the two or more substrates, in which diffraction grating 9 is formed, may be stacked. As illustrated in FIG. 3B, diffraction grating 10 made by processing both sides of the substrate may be used. For example, a first diffraction grating may be formed on one surface side of the substrate, and a second diffraction grating may be formed on the other surface side of the substrate as displaced by ¼-pitch in the cyclic direction. When the diffraction gratings are stacked, while it is desirable to stack the processed substrate so that the diffraction gratings contact with each other, the diffraction gratings may be apart from each other. When the diffraction gratings are apart from each other, the substrates are stacked so as to be parallel to each other.

An alignment mark may be previously made in the substrate to execute the alignment. As other method for the alignment, the alignment can be executed by expansion-observing the diffraction grating with an X-ray microscope. The alignment may be executed as observing a self-image obtained by the Talbot effect by irradiating the X-ray which can be spatially interfered. The phase grating may be fixed after the alignment, alternatively an X-ray phase image may be directly observed. The phase grating can be fixed with adhesive material such as epoxy resin, gold-gold junction, mechanical fixing using a clamp, or the like.

It is desirable to use, as the substrate, material in which the X-ray absorption is smaller when the X-ray is irradiated. When a shape is thin pate-like, and both sides are mirror finished surfaces, the contrast becomes preferable. For example, the following material can be used: A wafer such as Si, GaAs, Ge, and InP, and a glass substrate. While the X-ray absorption is larger than that of Si, a resin substrate can be also used, such as polycarbonate (PC), polyimide (PI), polymethylmethacrylate (PMMA).

The following methods can be used to form the diffraction grating: a photolithography method, a dry etching method, a variety of film forming methods such as spattering, vapor deposition, CVD, electroless plating, and electroplating, and a nanoimprint. That is, after a resist pattern is formed by the photolithography method, the substrate may be processed by the dry etching method or a wet-etching method, alternatively, the diffraction grating can also be provided on the substrate by a lift-off method. The substrate or material film-formed on the substrate may be processed by the nanoimprint.

The one-dimensional phase grating of the present exemplary embodiment can be used as the Talbot interferometer by combining with the X-ray source which can be spatially interfered, and the detector. In such a case, an output may be detected by using the detector after moiré fringes are formed by using an absorption grating. An imaging apparatus for an X-ray phase image of the present invention is incorporated in a gantry used in a conventional computed tomography system, thereby, an X-ray phase tomography image of a patient can be obtained.

(Exemplary Embodiment 2)

In the embodiment 2, an exemplary configuration of a two-dimensional phase grating, in which a stacking direction is different from that of the above exemplary embodiment 1, will be described. FIG. 4A illustrates a view for describing an exemplary configuration of the two-dimensional phase grating in the present exemplary embodiment.

Figure 4B:
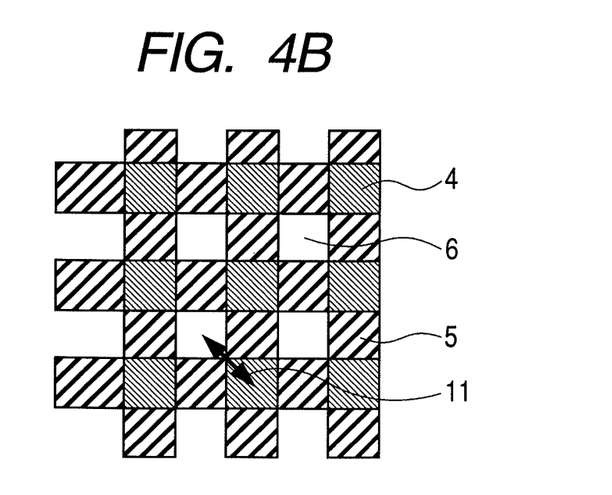
FIG. 4B illustrates a phase difference of the X-ray transmitting the phase grating illustrated in FIG. 4A.

The two-dimensional phase grating according to the present exemplary embodiment is formed as stacked so that a cyclic direction of a first layer of a diffraction grating 2 (a first diffraction grating), and a cyclic direction of a second layer of a diffraction grating 3 (a second diffraction grating) are orthogonal to each other. The first and second diffraction gratings are structured so that the projection part whose thickness is formed so that the in-coming X-ray transmits with the phase π-shifted, and the aperture part with the same aperture width as a width of projection part are cyclically arranged, and the width of the projection part and the aperture width are equal to each other. Here, when an X-ray 1 in-comes from a direction in which the diffraction grating is stacked, a phase change of the in-coming X-ray 1 by the phase grating becomes as illustrated in FIG. 4B. In such a case, a pitch 11 of the above two-dimensional phase grating is in a diagonal direction of the phase grating illustrated in FIG. 4B, and is narrowed as compared with a pitch of each diffraction grating.

Each diffraction grating configured in the two-dimensional phase grating according to the present exemplary embodiment is not limited to a line-like type, and may be also the diffraction grating obtained by multilayering the diffraction grating with the two-dimensional structure. The diffraction grating with the two-dimensional structure can, for example, correspond to a checker grating-like diffraction grating. Here, "the checker grating-like" means a structure in which the square-shaped (square or rectangle) aperture part is cyclically arranged in a first direction and a second direction orthogonal to the first direction. "Orthogonal line-like" means a structure in which a plurality of lines, which are parallel to each other and whose distance is equal, are orthogonally arranged. A projection structure may correspond to any one of a line part and an inter-line part.

Figure 5B:
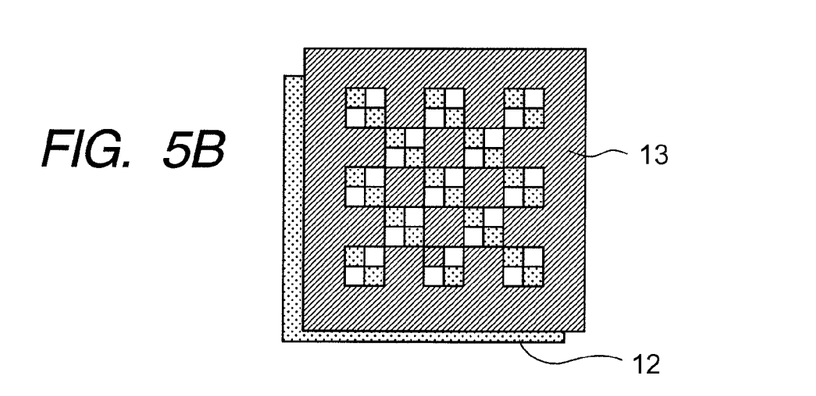
FIG. 5B is a view obtained by viewing the two-dimensional phase grating from an X-ray source in the exemplary embodiment 2 of the present invention.
Figure 5C:
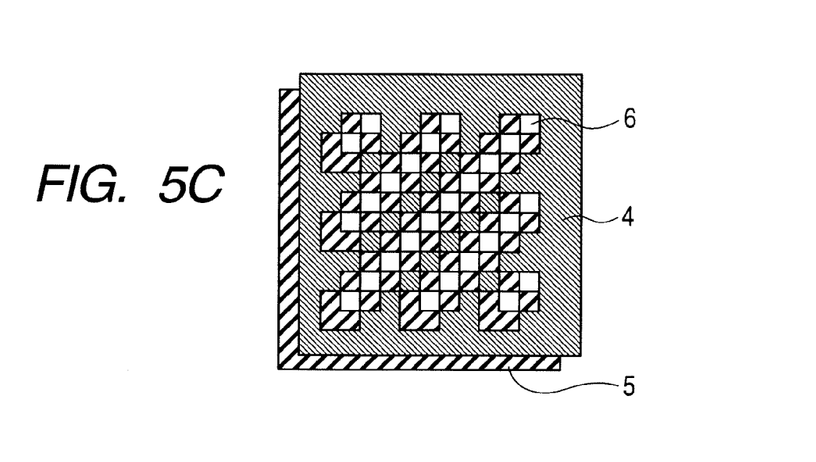
FIG. 5C is a view illustrating a phase difference of the X-ray transmitting the two-dimensional phase grating illustrated in FIG. 5A.
Figure 6:
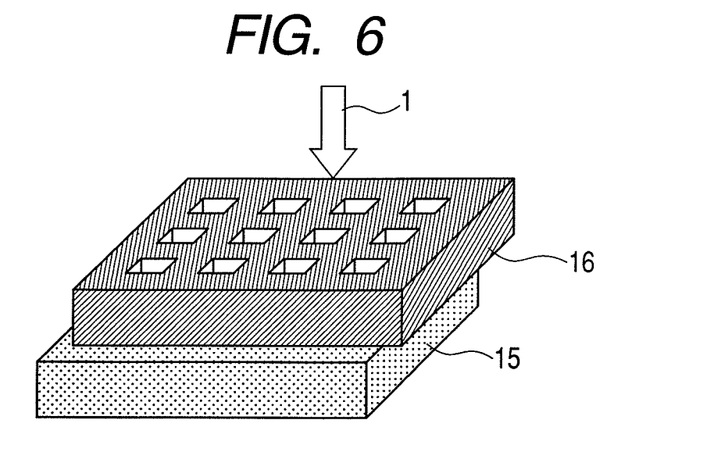
FIG. 6 is a view illustrating an exemplary configuration in which a set of the line-like diffraction gratings are arranged orthogonal to each other in the exemplary embodiment 2 of the present invention.

In the present exemplary embodiment, when the diffraction grating is multilayered, the diffraction grating with the two-dimensional structure is displaced in the cyclic direction and a direction orthogonal to the cyclic direction, thereby, a multilayer structure is made. FIG. 5A illustrates a perspective view of the diffraction grating in which a second layer of checker grating-like diffraction grating 13 is formed on a first layer of checker grating-like diffraction grating 12. In FIG. 5A, apertures 14 are two-dimensionally arranged on the second layer of checker grating-like diffraction grating 13, and FIG. 5B illustrates an upper side view thereof. In this example, the diffraction grating is stacked as displaced by ¼ in the cyclic direction (first direction) and the direction orthogonal to the cyclic direction (second direction) respectively. As described above, the phase of the X-ray, whose phase difference is 2π, is the same as that of the X-ray whose phase is not changed. Specifically, as shown in FIG. 5C, the one-dimensional phase grating includes an area 6 in which the phase of the incoming X-ray is not changed, an area 5 in which the phase is π-shifted, and an area 4 in which the phase is 2π-shifted. Thus, as illustrated in FIG. 5C, the phase grating for the X-ray phase imaging, whose pitch is narrower than that of each diffraction grating, can be obtained. As illustrated in FIG. 6, the diffraction grating with the two-dimensional structure may be obtained by stacking the second layer of diffraction grating 16 upon the first layer of diffraction grating 15, in which the square-shaped aperture parts are two-dimensionally arranged in the first direction and the second direction orthogonal to the first direction, as displaced by ¼-pitch in the first direction and the second direction respectively.

(Exemplary Embodiment 3)

Figure 7A:
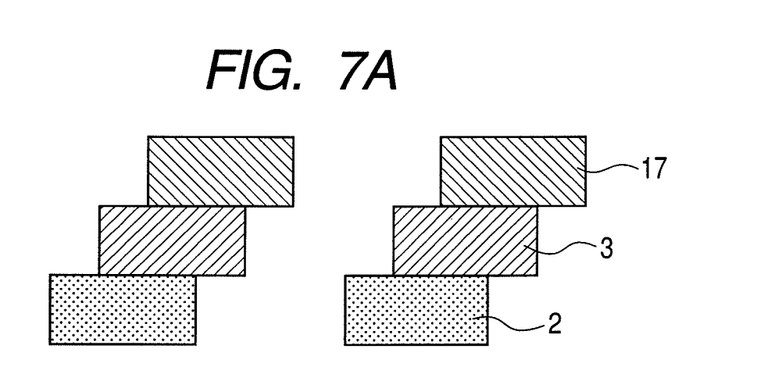
FIG. 7A is a view describing an exemplary configuration of the phase grating used for the X-ray phase imaging, which is configured with three layers of the diffraction gratings in an exemplary embodiment 3 of the present invention.

In the exemplary embodiment 3, an exemplary configuration of the phase grating used for the X-ray phase imaging, in which three or more layers of the diffraction gratings are stacked to be multilayered, will be described. FIG. 7A illustrates the phase grating used for the X-ray phase imaging, which is configured with the three layers of the diffraction gratings, in the present exemplary embodiment.

Figure 7B:
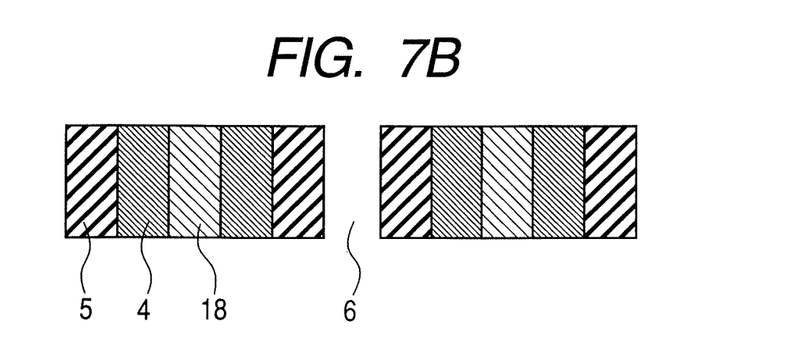
FIG. 7B is a view illustrating a phase difference of the X-ray transmitting the phase grating illustrated in FIG. 7A.

The phase grating according to the present exemplary embodiment is configured so that such diffraction gratings are stacked as displaced by ⅙-pitch in the cyclic direction for the diffraction grating of the lower layer. For example, the phase grating is configured by stacking the second layer of the diffraction grating displaced by ⅙-pitch, and the third layer of the diffraction grating 17 further displaced by ⅙-pitch for the first layer of the diffraction grating 2. The structure of each diffraction grating is constructed in a manner that the projection part whose thickness is formed so that the in-coming X-ray transmits with the phase π-shifted, and the aperture part with the same aperture width as a width of the projection part, are cyclically and one-dimensionally arranged, and the width of the projection part and the aperture width are equal to each other. FIG. 7B illustrates an appearance in which a phase change of the X-ray transmitting the phase grating according to the present exemplary embodiment is viewed from a vertical direction of the substrate. Since that the phase of the X-ray is 3π-shifted is equal to that the phase is π-shifted, the phase of an area 5, in which the phase is π-shifted, is equal to the phase of an area 18, in which the phase is 3π-shifted. The phases of the X-ray are equal to each other in both of an area 4 in which the phase is 2π-shifted, and an area 6 in which the X-ray transmits without the phase changed. Thus, the pitch of the area, in which the phase of the X-ray is modulated, can be narrowed as compared with the pitch of each diffraction grating. That is, by stacking three layers of the diffraction gratings, the pitch of the phase grating for the X-ray phase imaging can be reduced to ⅓ of the pitch of each diffraction grating.

While such a case has been described in the present exemplary embodiment that three layers of the diffraction gratings are stacked, the phase grating may be configured by stacking "n" (n>=2) pieces of the diffraction gratings. When the phase grating is made by stacking "n" pieces of the diffraction gratings, the projection part of the m-th (M=2, 3, . . . n) diffraction grating is formed as displaced by 1/(2n)-pitch in the cyclic direction of the one-dimensional arrangement for the projection part of the (m−1)-th stacked diffraction grating. Because n pieces of layers of the diffraction gratings are stacked, the pitch of the phase grating for the X-ray phase imaging becomes 1/n of the pitch of each diffraction grating, and the pitch is narrowed.

While the one-dimensional phase grating in which three or more layers of the diffraction gratings are stacked has been described in the present exemplary embodiment, the two-dimensional phase grating may be made by stacking three or more layers of the diffraction gratings.

In the exemplary embodiments of the present invention, by using the phase grating used for the X-ray phase imaging of any of the above exemplary embodiments 1 to 3 in the imaging apparatus for the X-ray phase contrast image, the imaging apparatus can be realized, in which the X-ray phase contrast image can be imaged. Further, an X-ray computed tomography system can be realized, which includes such an imaging apparatus for the X-ray phase contrast image.

[Embodiment]

An embodiment of the present invention will be described below.

[Embodiment 1]

In the embodiment 1, an exemplary configuration of the line-like diffraction grating will be described, in which the line-like projection structures (projection parts) which are parallel to each other as the one-dimensional phase grating, and the aperture part with the same aperture width as a width of the projection part, are cyclically arranged. In the present embodiment, first, a surface of a silicon wafer of diameter: 4 inch, both sides-polished, and thickness: 200 μm is resist-coated, followed by making a resist pattern of line width: 2 μm, and distance: 2 μm in a 60 mm square area by the photolithography method. Next, the following process is executed by Deep Reactive Ion Etching (hereinafter, described as Deep-RIE). That is, slit structure of width: 2 μm, distance: 2 μm, and depth: 29 μm is made, followed by eliminating a resist (refer to FIG. 2B). Next, the same pattern is made on two wafer surfaces. The two processed silicon wafers are stuck together so that the patterns contact to each other (refer to FIG. 3A). In this case, the slit structures are caused to be parallel to each other, and a displacement of the slit is caused to be 1 μm in the cyclic direction. In the alignment, the X-ray of 20 keV is irradiated from a vertical structure of the wafer, and a detector is arranged at a location of $(d^2/8\lambda)=8$ mm from the phase grating, thereby, a dark-light pattern of 1 μm pitch is obtained. By the above method, the phase grating for the X-ray phase imaging can be made, which can cause, by 2 μm pitch, the in-coming X-ray to transmit with the phase π-shifted. This phase grating is used as the phase grating for the Talbot interferometer, and the absorption grating of 1 μm pitch is arranged in parallel to the phase grating at a location which is 8 mm apart from the phase grating, thereby, the observation for the X-ray phase image can be realized.

[Embodiment 2]

In the embodiment 2, an exemplary configuration will be described, in which the two-dimensional phase grating is formed with the checker grating-like diffraction grating by using the same substrate. In the present embodiment, first, after a surface of the silicon wafer of diameter: 4-inch, both sides-polished, and thickness: 200 μm is resist-coated, a slit-like resist pattern of line width: 2 μm, and distance: 2 μm is made in a 60 mm square area by the photolithography method. In this case, circular resist patterns of 10 μm Φ are also made at four corners of the slit at the same time. Next, by the Deep-RIE, the slit structure of width: 2 μm, distance: 2 μm, and depth: 29 μm is made, and the circular patterns of 10 μm Φ are made at four corners of the slit. After that, the resist is eliminated.

Next, a backside of a side in which the pattern is formed, is resist-coated, and the four circular patterns of 10 μm Φ are designated as an alignment mark, and the resist pattern is formed by the photolithography method. Thereby, the slit-like resist pattern of line width: 2 μm, and distance: 2 μm is formed so as to be orthogonal to a Si slit pattern which is previously formed by the dry etching method. After that, the slit structure of width: 2 μm, distance: 2 μm, and depth: 29 μm is also formed on the back side by the Deep-RIE. Thereby, the two-dimensional phase grating can be obtained, which is configured with the checker grating-like diffraction gratings whose pitch is 2.8 μm, and which makes an angle of 45 degrees to the line-like grating.

[Embodiment 3]

In the embodiment 3, an exemplary configuration will be described, in which the two-dimensional phase grating is formed with the checker grating-like diffraction grating by using the different substrate. In the present embodiment, first, after a surface of the silicon wafer of diameter: 4-inch, both sides-polished, and thickness: 200 μm is resist-coated, the aperture part of side: 4 μm is made in a checker grating-like pattern in a 60 mm square area by the photolithography method. Next, the silicon wafer is etched up to depth: 29 μm. The same patterns are made on the surfaces of the two wafer (FIG. 5A). The two processed silicon wafers are stuck together so that the patterns contact each other. In this case, vertical lines and horizontal lines of a square are caused to be parallel to each other between the two wafers, and the two wafers are stacked as displaced by 2 μm in a vertical line direction and a horizontal line direction. Thereby, the checker grating (side: 2 μm)-like phase grating can be obtained.

[Embodiment 4]

In the embodiment 4, an exemplary configuration will be described, in which the phase grating is formed by stacking three layers of the diffraction gratings. In the present embodiment, first, after a surface of the silicon wafer of diameter: 4-inch, both sides-polished, and thickness: 150 μm is coated with the polymethylmethacrylate (PMMA), an uneven pattern of line width: 9 μm, distance: 9 μm, and depth: 29 μm is made by a UV nanoimprint in a 60 mm square area. Thereby, the same patterns are made in the three silicon wafer. Next, the two processed silicon wafers are stuck together so that the patterns contact each other. In this case, the slit structures are caused to be parallel to each other, and a displacement of the slit is caused to be ⅓-pitch, that is, 3 μm in the cyclic direction.

Next, the remaining silicon wafer is stuck together to the two stuck substrates. In the alignment for the third substrate, all of the slit structures are caused to be parallel to each other by expansion-observing the phase grating with the X-ray microscope. In the third substrate, a displacement of the slit is caused to be 3 μm in the cyclic direction from the slit structure formed in the substrate contacting the third substrate. In this case, the slit structures formed in the substrates of both sides are caused not to be overlapped for the transmitting X-ray. FIG. 7B illustrates a cross-section view in this case. When the X-ray of 20 keV is irradiated from a vertical direction to the wafer after the stacking, the dark-light pattern of 3 μm pitch is obtained at a location of $d^2/(8\lambda)=72$ mm (Talbot length) from the phase grating. Thereby, by stacking three layers of the patterns of line width: 9 μm, and distance: 9 μm, the phase grating of π-shifting by 6 μm pitch can be obtained.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-064709, filed Mar. 13, 2008, which is hereby incorporated by reference herein in its entirety.

The invention claimed is:

1. A phase grating used for X-ray phase imaging, comprising:
   a first diffraction grating in which a first projection part whose thickness is formed so that an in-coming X-ray transmits with a phase π-shifted, and a first aperture part with a same aperture width as a width of the first projection part, are cyclically arranged in a cyclic direction; and
   a second diffraction grating in which a second projection part with a same width as the width of the first projection part, and a second aperture part with a same aperture width as the aperture width of the first aperture part, are cyclically arranged in a cyclic direction,
   wherein
   the cyclic direction of the first diffraction grating is the cyclic direction of the second diffraction grating, and
   the second diffraction grating is formed as displaced by ¼-pitch on the first diffraction grating.

2. The phase grating according to claim 1, further comprising:
   a substrate,
   wherein
   the first diffraction grating is formed on one side of the substrate, and
   the second diffraction grating is formed on the other side of the substrate, of the first diffraction grating as displaced by ¼-pitch on the first diffraction grating.

3. The phase grating according to claim 1, wherein
   the first diffraction grating includes square-shaped first aperture parts which are two-dimensionally and cyclically arranged in a first direction and a second direction orthogonal to the first direction,
   the second diffraction grating includes the square-shaped second aperture parts which are two-dimensionally and cyclically arranged in the first direction and in the second direction, and
   the second diffraction grating is formed such that the second aperture parts are displaced by ¼-pitch in the first direction and by ¼-pitch in the second direction with respect to the first aperture parts.

4. An imaging apparatus for X-ray phase imaging, comprising:
   the phase grating according to claim 1; and
   a detector.

5. A phase grating used for X-ray phase imaging, comprising:
   a first diffraction grating in which a first projection part whose thickness is formed so that an in-coming X-ray transmits with a phase π-shifted, and a first aperture part with a same aperture width as a width of the first projection part, are cyclically arranged in a cyclic direction; and
   a second diffraction grating in which a second projection part with a same width as the width of the first projection part, and a second aperture part with a same aperture width as the aperture width of the first aperture part, are cyclically arranged in a cyclic direction,
   wherein the cyclic direction of the first diffraction grating and the cyclic direction of the second diffraction grating are orthogonal to each other.

6. An imaging apparatus for X-ray phase imaging, comprising:
   the phase grating according to claim 5; and
   a detector.

7. A phase grating used for X-ray phase imaging, comprising:
   n (n>=2) pieces of diffraction gratings stacked, each of the diffraction gratings including a projection part whose thickness is formed so that an in-coming X-ray transmits with a phase π-shifted, and an aperture part with a same width as a width of the projection part are cyclically arranged in a cyclic direction,
   wherein the projection part of the m-th (m=2, 3, . . . n) stacked diffraction grating is formed as displaced by $1/(2n)$-pitch in the cyclic direction for the projection part of the (m−1)-th stacked diffraction grating.

8. An imaging apparatus for X-ray phase imaging, comprising:
   the phase grating according to claim 7; and
   a detector.

9. A phase grating used for X-ray phase imaging, comprising:
   a first diffraction grating in which a first projection part whose thickness is formed so that an in-coming X-ray transmits with a phase π-shifted, and a first concave part with a same width as a width of the first projection part, are cyclically arranged in a cyclic direction; and
   a second diffraction grating in which a second projection part with a same width as the width of the first projection part, and a second concave part with a same width as the width of the first concave part, are cyclically arranged in a cyclic direction,
   wherein
   the cyclic direction of the first diffraction grating is the cyclic direction of the second diffraction grating, and
   the second diffraction grating is formed as displaced by ¼-pitch on the first diffraction grating.

10. The phase grating according to claim 9, further comprising:
    a substrate,
    wherein
    the first diffraction grating is formed on one side of the substrate, and
    the second diffraction grating is formed on the other side of the substrate, of the first diffraction grating as displaced by ¼-pitch on the first diffraction grating.

11. An imaging apparatus for X-ray phase imaging, comprising:
    the phase grating according to claim 9; and
    a detector.

12. A phase grating used for X-ray phase imaging, comprising:

a first diffraction grating in which a first projection part whose thickness is formed so that an in-coming X-ray transmits with a phase π-shifted, and a first concave part with a same width as a width of the first projection part, are cyclically arranged in a cyclic direction; and a second diffraction grating in which a second projection part with a same width as the width of the first projection part, and a second concave part with a same width as the width of the first concave part, are cyclically arranged in a cyclic direction, wherein the cyclic direction of the first diffraction grating and the cyclic direction of the second diffraction grating are orthogonal to each other.

13. An imaging apparatus for X-ray phase imaging, comprising:

the phase grating according to claim 12; and a detector.

14. A phase grating used for X-ray phase imaging, comprising:

n (n>=2) pieces of diffraction gratings stacked, each of the diffraction gratings including a projection part whose thickness is formed so that an in-coming X-ray transmits with a phase π-shifted, and a concave part with a same width as a width of the projection part are cyclically arranged in a cyclic direction, wherein the projection part of the m-th (m=2, 3, ... n) stacked diffraction grating is formed as displaced by 1/(2n)-pitch in the cyclic direction for the projection part of the (m−1)-th stacked diffraction grating.

15. An imaging apparatus for X-ray phase imaging, comprising:

the phase grating according to claim 14; and a detector.

* * * * *